United States Patent [19]

Roffia et al.

[11] 4,356,319

[45] Oct. 26, 1982

[54] METHOD OF RECOVERING IN ACTIVE FORM THE CATALYST FOR THE TEREPHTHALIC ACID SYNTHESIS

[75] Inventors: Paolo Roffia, Saronno; Pierangelo Calini, Rho; Sergio Tonti, Venezia Mestre, all of Italy

[73] Assignee: Montedison, S.p.A., Milan, Italy

[21] Appl. No.: 226,382

[22] Filed: Jan. 19, 1981

[30] Foreign Application Priority Data

Jan. 23, 1980 [IT] Italy .............................. 193393 A/80

[51] Int. Cl.³ .................... C07C 51/29; C07C 51/265; B01J 31/40

[52] U.S. Cl. ................................. 562/414; 252/413; 252/414; 252/420

[58] Field of Search ....................... 252/413, 414, 420; 562/414, 485; 423/49, 150

[56] References Cited

U.S. PATENT DOCUMENTS 2,964,559 12/1960 Burney ................................ 562/414
3,624,145 11/1971 Brinn ................................... 562/485
3,950,409 4/1976 Yokota et al. ...................... 562/414
4,185,073 1/1980 Marsh et al. ....................... 562/414

FOREIGN PATENT DOCUMENTS 54-126686 10/1979 Japan .

Primary Examiner—P. E. Konopka
Attorney, Agent, or Firm—Morgan, Finnegan, Pine, Foley & Lee

[57] ABSTRACT

A method of recovering the catalyst in active form from the acetic mother liquors from the synthesis of terephthalic acid. From said mother liquors, after removal of water, there is removed by evaporation an amount of from 70 to 90% of the $CH_3COOH$ present therein. The concentrated liquor is cooled below 60° C. and the solid which precipitates is collected and recycled for reuse in the systhesis. The liquid phase is extracted with water or with an aqueous acetic acid solution in the presence of particular coadjuvants such as isobutyl acetate, and the aqueous phase, which contains the recovered catalyst, is recycled to the original synthesis.

8 Claims, 1 Drawing Figure

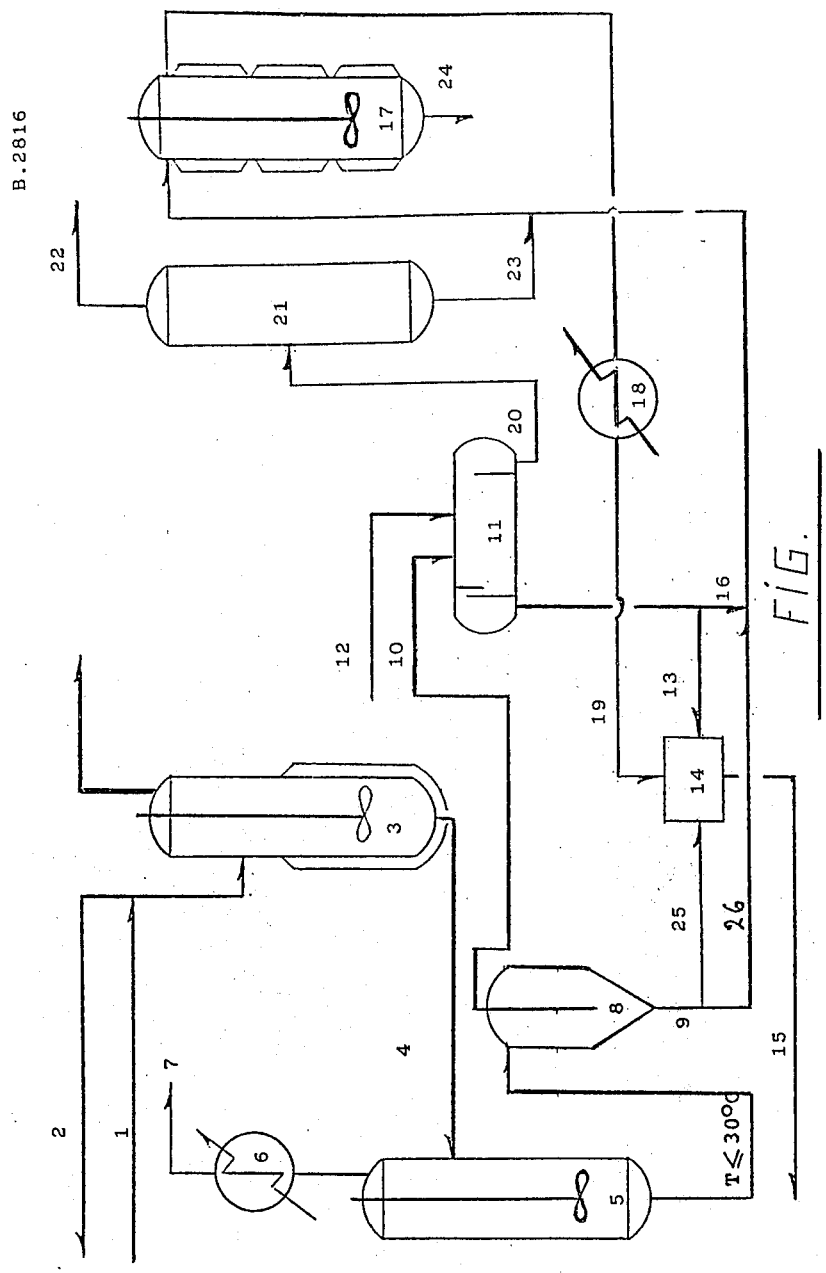

METHOD OF RECOVERING IN ACTIVE FORM THE CATALYST FOR THE TEREPHTHALIC ACID SYNTHESIS

BACKGROUND OF THE INVENTION

It is known that the terephthalic acid synthesis is effected by oxidizing p-xylene with oxygen, in an acetic solution and in the presence of a catalyst based on manganese, cobalt and bromine, the terephthalic acid being separated in solid form from the reaction mother liquor. It is also known how to recover the catalyst components from the mother liquor, by reducing the $H_2O$ content of the mother liquor and by recycling to oxidation at least 50% of the so dehydrated mother liquor containing the catalyst components; the remaining portion of the dehydrated liquor is then concentrated by evaporation and the concentrate passes to an incinerator wherefrom combustion products having a high content of catalyst components are produced. It is known by experience that this method is not quite satisfactory. In fact, it is possible to recycle at the most, on a commercial scale, 60% of the dehydrated liquor. Thus, there results that at least 40% of the catalyst is in the form of ashes from which it is difficult and complex to recover the catalyst.

If higher amounts of dehydrated liquor are recycled, the build up of organic impurities reaches inadmissible levels and the catalyst activity is remarkably reduced. Said impurities, consisting for example of isophthalic acid, need to be eliminated, both because they are no longer convertible into terephthalic acid and because they negatively affect the reaction.

OBJECTS OF THE INVENTION

It is an object of the invention in a terephthalic acid synthesis to recover the highest possible amount of catalyst components in a simple and practical way thus reducing to a minimum the residual amounts intended for incineration.

Further objects will appear from the description given hereinbelow.

GENERAL DESCRIPTION OF THE INVENTION

In its most general form the present invention relates to a method of recovering in active form the catalyst from at least a portion of the dehydrated acetic mother liquor from the terephthalic acid synthesis after concentration of said portion until an amount of from 70 to 90% of acetic acid is removed. In the process of this invention, the concentrated mother liquor is cooled down below 60° C., preferably between 15° to 50° C., thus causing a solid phase to precipitate. Then, the solid phase is separated from the remaining liquid phase containing organic impurities. The solid phase is partially or wholly recycled to the zone where the terephthalic acid synthesis occurs, the remaining liquid phase being extracted with water or with aqueous-acetic solutions in the presence of a coadjuvant selected from the group consisting of paraxylene, isobutyl acetate and secondary butyl acetate, whereupon the aqueous phase is recycled to the synthesis zone. Some water, which forms during the oxidation of paraxylene, is still present in said liquid phase, but if no coadjuvant is added the extraction is practically impossible due to the low of separation rate. This method permits to separate the catalyst components from almost all the polluting organic by-products which otherwise would follow the catalyst in the recycle; conversely, the useful intermediates such as paratoluic acid and 4-carboxybenzaldehyde (4-CBA), capable of being converted into terephthalic acid, are recovered for the most part in the solid phase which precipitates and is advantageously recycled to the synthesis zone.

The addition of the concentrated liquor, generally containing, besides acetic acid, a $H_2O$ amount ranging from 2 to 6% by weight, of a coadjuvant compatible with the paraxylene oxidation, such as p-xylene or isobutyl acetate or secondary butyl acetate, preferably in admixture with integrative water amounts, causes a separation; a heavy aqueous acetic phase, containing the catalyst components and practically free from oxidation by-products separates from a lighter organic phase containing such by-products, the remaining portion of $CH_3COOH$ and the added coadjuvant, which may be considered as an extracting agent for the impurities. The catalyst system can be recovered with yields higher than 80% for all the components present (Co, Br, Mn). It retains its activity unchanged and can be directly recycled, either wholly or in part, to the oxidation reaction.

The present method affords many advantages. It eliminates the problem of the build up of the by-products which are real poisons for the catalyst. The present method renders unlimitedly repetitive the catalyst recycle and brings the recycle to high values without affecting the oxidation or the product quality. The interruption of the distillation of the reaction solvent (acetic acid), after it has been evaporated for 70-90%, permits the recovery of the terephthalic acid escaping from the centrifuges and the oxidation intermediates, which are present as solids in the distillation tail products and are free from the by-products which remain in the liquid phase so that it is possible to recycle terephthalic acid and intermediates to further improve the yields.

The operative conditions for oxidizing para-xylene are known and the present invention can be applied to all the processes for catalytically oxidizing p-xylene. Thus, the present invention can be applied to processes operating at different temperatures, pressures and concentrations, as well as to processes employing catalyst components other than Co and Mn, such as e.g. cerium, titanium, chromium and barium.

This invention is applicable to all the processes equivalent to the oxidation of p-xylene, such as the oxidations of toluene to benzoic acid, of metaxylene to isophthalic acid, of orthoxylene to o-phthalic acid or to phthalic anhydride and in general to the oxidations of mono- and polyalkyl substituted aromatic compounds. In these cases the most suitable coadjuvants may be: toluene in the case of benzoic acid, metaxylene in the case of isophthalic acid, and orthoxylene in the case of phthalic anhydride. Other suitable coadjuvants, both in the case of terephthalic acid and in the case of the other acids or aromatic anhydrides, are the aliphatic hydrocarbons with 6 to 12 carbon atoms, the aromatic mono- and poly alkyl substituted hydrocarbons, the esters of aliphatic and aromatic acids and the aliphatic ketones. When the coadjuvant is paraxylene, it can be recovered along with acetic acid by evaporation of the solution containing the organic by-products which are so removed from the productive cycle, without any catalyst losses, and are sent to the incinerator or to the biological purification vats. Another coadjuvant compatible with the terephthalic synthesis is isobutyl acetate, which is used as an azeotroping agent during the acetic acid dehydration. After demixing, enhanced by isobutyl acetate, the catalyst is ready, in the aqueous phase and in an active form, for being recycled to the synthesis, while the isobutylacetic phase, containing the reaction by products, $CH_3COOH$ and ester, is distilled; the distillate can be sent to the dehydration column of $CH_3COOH$. Isobutyl acetate can be substituted by secondary butyl acetate, which can be recycled, after evaporation and together with $CH_3COOH$, to the oxidation reaction, where it is oxidized, with a rather good selectivity, to acetic acid, so making up for the $CH_3COOH$ used during oxidation.

For practicing the present invention it is possible to use all the known liquid-liquid extraction techniques operating either continuously or discontinuously and in one or more steps, depending on the process requirements and on the amount to be recycled. The extraction temperature may vary from the room temperature to boiling point of the coadjuvant, preferably from 20° to 80° C.; the coadjuvant amount preferably ranges from 0.5 kg to 2.5 kg per kg of solution to be extracted.

A better understanding of the invention will be had by reference to the accompanying drawing, wherein the FIGURE is a schematic diagram of a continuous process for the production of terephthalic acid, incorporating therein the catalyst recovery process of the present invention.

SPECIFIC DESCRIPTION OF THE INVENTION

The following examples are given to illustrate the present invention, without being, however, a limitation thereof.

EXAMPLE 1

Part A

Oxidation of p-xylene and Recovery of the Catalyst from the Concentrated Liquor, 720 g of $CH_3COOH$ containing 0.67 g tetrahydrated cobalt acetate, 1.99 g of tetrahydrated manganese acetate and 1.23 $cm^3$ of an aqueous solution of 40% by weight of HBr were charged into a titanium autoclave having a 2-liter capacity, thermoregulated and equipped with a stirrer and a reflux condenser. The solution was heated to 220° C. maintaining a pressure of 24 $kg/cm^2$ under nitrogen. The stirrer was made to rotate at 600 rpm and 200 $cm^3$ of a solution of 79% by weight of p-xylene in acetic acid were fed; simultaneously, such an amount of air was fed, as to increase the oxygen concentration in the purged gases—which are continuously fed in order to maintain the pressure at the initial value of 24 $kg/cm^2$—up to 2-2.5% by volume. After 2 hours it was cooled down and a suspension of terephthalic acid was recovered, which was separated from the mother liquor by filtration, was washed with $CH_3COOH$ and with $H_2O$ and was dried in an oven at 100° C. under vacuum. The yield, based on the paraxylene reactant was 94.8%. The analysis under a polarograph revealed 400 ppm of 4-CBA; the product transmittance, determined on 15% solutions in double normal NaOH at 340 nm, was 78%. The mother liquor recovered after filtration was distilled and, after evaporation of about 90% of the solvent, the residue was distilled at 25° C., thus causing a solid phase to precipitate, which consisted mainly of terephthalic acid (68% by weight), p-toluic acid (15%), 4-CBA (10%) and benzoic acid (3%) and which contained also 30% of the manganese and 15% of the cobalt used during the test. It was filtered and to the filtrate, containing most of the catalyst and the undesired by-products of the synthesis, 100 g of p-xylene were added; a phase separation with the following results was obtained:

| Components | % by weight | | Distribution (%) | |
|---|---|---|---|---|
| | heavy phase | light phase | heavy phase | light phase |
| $H_2O$ | 18.14 | — | 100 | — |
| p-xylene | 9.79 | 57.82 | 1.7 | 97.3 |
| $CH_3COOH$ | 67.84 | 39.40 | 22 | 78 |
| Co | 0.44 | 0.008 | 90 | 10 |
| Mn | 1.082 | 0.0083 | 95.5 | 4.5 |
| Br | 1.982 | 0.0189 | 94.5 | 5.5 |
| organic by-products | 0.696 | 2.738 | 4 | 96 |

The heavy phase (27.56 g), containing most of the catalyst, was recycled to oxidation, operating as described in part B; the light phase, consisting of $CH_3COOH$ and p-xylene, was evaporated in order to recover the volatile components. The residue, consisting of a minimum part of catalyst and of the by-products, was sent to the destructive treatments. As shown from the results reported in the table, the method is extremely effective in selectively isolating almost the totality of the catalyst components in a heavy aqueous acetic phase which contained a minimum percentage (4%) of the impurities originally present and which was recyclable to oxidation without any drawbacks. On the other hand the light phase contained almost the totality of the initial impurities besides small residual amounts of catalyst components.

Part B

Re-utilization of the Recovered Catalyst in a Second Oxidation

To 27.56 g of the abovesaid heavy phase were added 0.66 g of $Mn(CH_3COO^-)_2.4H_2O$ 0.157 g of Co $(CH_3OO^-)_2.4H_2O$ and 0.242 $cm^3$ of an aqueous solution at 40% by weight of HBr and the resulting composition was charged into the autoclave along with 700 g of $CH_3COOH$. The resulting mixture was heated to 220° C. at 24 $kg/cm^2$ and was stirred at 600 rpm and a solution of 79% by weight of p-xylene in $CH_3COOH$ was fed at a flowrate of 200 $cm^3$/hour. Air was continuously fed by withdrawing purge gases containing 2 to 2.5% volume of $O_2$, the pressure being maintained at 24 $kg/cm^2$. After 2 hours it was cooled down and the terephthalic acid was recovered by filtration, washed with $CH_3COOH$ and $H_2O$ and dried in an oven at 100° C. under vacuum. The yields were 94.8%. The 4-CBA content was 420 ppm and the transmittance at 340 nm was 77%. It was noticed that, with a catalyst made up of about 80% of recovered catalyst and only of 20% of fresh replenished catalyst, the terephthalic acid yield and quality were fully equivalent to the ones obtained with an all fresh catalyst as in Part A.

EXAMPLE 2 (Comparative)

Direct Recycle of Dehydrated Mother Liquor

Oxidation was performed as in Example 1 (Part A) and the same results were obtained. The mother liquor recovered by filtration of terephthalic acid underwent a distillation, in order to remove the reaction water, and the dehydrated solution containing CH₃COOH, catalyst and reaction intermediates, was combined with 0.185 cm³ of an aqueous solution of 40% by weight of HBr to make up for the losses. The solution (725 g) was poured again into the autoclave and oxidation was repeated according to the same operative conditions. After cooling, terephthalic acid was recovered by filtration, washed and dried. The yields were 95.4% while the 4-CBA content was 750 ppm and the transmittance at 340 nm (of a 15% solution in double normal KOH) was 60%.

EXAMPLE 3

Example 1 was repeated and from the reaction mother liquors it was possible to recover, after evaporation, 7.4 g of a solid phase consisting of terephthalic acid, reaction intermediates and part of the catalyst. By adding 100 g of paraxylene to the remaining solution, 25 g of a heavy phase were obtained, which contained 66% of charged manganese, 74% of charged cobalt and 85% of charged bromine. Both the solid and the heavy phase were collected together, were combined with 0.0796 g of Mn (CH₃COO⁻)₂.4H₂O, 0.0737 g of Co (CH₃COO⁻)₂.4H₂O and 0.177 cm³ of a solution of 40% by weight of HBr and were poured into the autoclave along with 700 g of CH₃COOH. A second oxidation was carried out at 220° C. and at 24 kg/cm², simultaneously conveying to the autoclave air and a 79% solution of p-xylene in CH₃COOH at a flowrate of 650 l/hour and of 200 cm³/hour respectively. After 2 hours it was cooled down and terephthalic acid was recovered according to usual condition and oven dried under vacuum at 100° C. The yield amounted to 96.2%, while the 4-CBA content was of 430 ppm; the terephthalic acid transmittance (at 340 nm in a 15% solution in double normal NaOH) was equal to 78%.

EXAMPLE 4

Part A 3,600 g of a solution containing 3.35 g of Co⁺⁺(CH₃COO⁻)₂. 4H₂O, 9,95 g of Mn⁺⁺(CH₃COO⁻)₂.4H₂O and 6.15 cm³ of an aqueous solution of 40% by weight of HBr were introduced into a titanium 5-liter autoclave, equipped with a stirrer, a heating jacket and a reflux condenser. The mixture was heated in a N₂ atmosphere of 220° C. and of 24 kg/cm² under stirring (600 rpm) and 1,000 cm³/h of a solution at 79% by weight of p-xylene in CH₃COOH were fed. At the same time, such an air amount was fed, as to keep the O₂ concentration in the purge gases between 2 and 2.5% by volume at constant pressure. After 2 hours it was cooled to 20° C. and terephthalic acid was separated by filtration. The product, washed with CH₃COOH and H₂O and dried in an oven at 100° C. under vacuum, contained 420 ppm of 4-CBA and had a transmittance (in NaOH, see Example 1) equal to 76%. The yield was 94.5%. The mother liquor was evaporated until 90% of CH₃COOH passed to the vapour phase; it was cooled down to 20° C., the solid phase was separated by filtration, whereupon 500 g of isobutyl acetate and 300 cm³ of H₂O were added to the filtrate; the compositions and the coefficients recorded on the following table were obtained.

| Components | % by weight heavy phase | % by weight light phase | Distribution (%) heavy phase | Distribution (%) light phase |
| --- | --- | --- | --- | --- |
| H₂O | 50.83 | 13.05 | 60.32 | 39.68 |
| Isobutyl acetate | 7 | 50.8 | 5.1 | 94.89 |
| CH₃COOH | 40.27 | 33.26 | 32.09 | 67.9 |
| Cobalt | 0.1711 | 0.0053 | 92.69 | 7.31 |
| Manganese | 0.3993 | 0.011 | 93.36 | 6.64 |
| Bromine | 0.7566 | 0.0138 | 95.53 | 4.47 |
| Iron | 0.0014 | 0.0002 | 73.21 | 26.79 |
| 4-CBA | 0.0476 | 0.13 | 12.50 | 87.5 |
| Benzoic acid | 0.192 | 1 | 6.99 | 93.01 |
| p-toluic acid | 0.157 | 1.1 | 5.28 | 94.7 |
| o-phthalic acid | 0.047 | 0.0667 | 21.7 | 78.3 |
| Terephthalic acid + isophthalic acid | 0.107 | 0.31 | 11.87 | 88.13 |
| toluene-dicarboxylic acid | 0.0167 | 0.203 | 3.1 | 96.9 |

Part B

To 220 g of the above-specified heavy phase were added 4.38 g of Mn⁺⁺(CH₃COO⁻)₂.4H₂O, 1.072 g of Co⁺⁺(CH₃COO⁻)₂. 0.4H₂O and 1.86 cm³ of hydrobromic solution at 40% by weight, and they were poured into the autoclave along with 3,500 g of CH₃COOH. Oxidation was then repeated under identical operative conditions, obtaining the following results:

yield=94.5%; 4-CBA=430 ppm; transmittance=75%.

EXAMPLE 5

Part A

Part A of Example 4 was repeated, but only 50% of the mother liquor was passed to the concentration, cooling, filtration and extraction operations. The remaining 50% was directly charged into the autoclave, without any treatment, for the second oxidation as per Part B.

Part B

50% of the untreated mother liquor, as hereinabove, and 110 g of the heavy phase, obtained by treating the concentrated liquor with 250 g of isobutyl acetate, were fed into the autoclave for the second oxidation. Manganese, cobalt and bromine were incorporated in an amount to restore concentrations and oxidation was repeated following identical conditions; the following results were obtained:

yield=95.2; 4-CBA=550 ppm; transmittance=72%

EXAMPLE 6 (Continuous Test)

Reference is made to the FIGURE: 1,000 parts by weight of dehydrated mother liquor obtained by oxidizing p-xylene as in Example 4, but with a shorter reaction time (30 minutes), by separating terephthalic acid through centrifugation and by distilling the mother liquor until the water content is reduced to 5% by weight were made to flow through line (1); 60% of the dehydrated liquor i.e. 600 parts, flowed back to the oxidation zone (line 2), while the remaining 40% passed to evaporator (3), from the top of which 327 parts by weight of vapours containing 94.5% by weight of CH₃COOH flowed out. 73 parts by weight of concentrated hot liquor (at about 118° C.) flowed (through line 4) to expansion tank (5), equipped with a reflux condenser (6) and a vacuum intake (7). The vacuum, created by means of a liquid ring pump, caused a rapid cooling to 40° C. of the concentrate and, as a result, the precipitation of a solid phase.

A hydrocyclone (8), or hydraulic cyclone, separated a thickened product (9), containing said solid phase, from 65 parts by weight of clarified liquid which passed (line 10) to extraction tank (11) to which 65 parts by weight of isobutyl acetate and 26 parts of $H_2O$ were fed (line 12); two phases were obtained, which corresponded to the following compositions and coefficients.

| Components | % by weight | | Distribution (%) | |
|---|---|---|---|---|
| | heavy phase | light phase | heavy phase | light phase |
| $H_2O$ | 37.69 | 13.01 | 42 | 58 |
| Isobutyl acetate | 7.29 | 50.26 | 3.5 | 96.5 |
| $CH_3COOH$ | 52.04 | 34.64 | 27.3 | 72.7 |
| Co | 0.20 | 0.011 | 82 | 18 |
| Mn | 0.47 | 0.026 | 82 | 18 |
| Br | 0.906 | 0.04 | 85 | 15 |
| Impurities | 0.79 | 2.01 | 9 | 91 |

95% of the heavy phase, containing nearly all the recovered catalyst, passed without any other treatments (line 13) to collection zone (14) and from here (line 15) to the oxidation reactor; 5% of the heavy phase was purged and passed (line 16) to apparatus (17), where substantially all the liquid present therein was brought to the vapour phase at a temperature of 130° C. The vapours leaving apparatus (17) from its head were condensed in heat exchanger (18) and passed (line 19) to collection zone (14); the extraction light phase (line 20) flowed (line 20) to a distillation column (21) which recovered isobutyl acetate and $CH_3COOH$ (line 22) from a tail product which contained almost the totality of the undesired impurities and which passed (line 23) to the above-described apparatus (17). The solid residue leaving the apparatus (17) through line (24), actually consisting of a screw feeder, passed to an incinerator, not appearing in the FIGURE. The solid phase separated in hydrocyclone (8) contained

| | (% by weight): | | |
|---|---|---|---|
| terephthalic acid | 58 | benzoic acid | 2 |
| p-toluic acid | 20 | isophthalic acid | 2 |
| 4-CBA | 25 | other matters | 2 |

95% of thickened product (9) passed to collection zone (14) through line (25), while the remaining 5% was purged (line 26) to apparatus (17), which recovered in the vapour phase all the liquid still present. A terephthalic acid containing 1,200 ppm of 4-CBA and having a transmittance (see Example 4) of 68% was obtained with yields of 95%.

EXAMPLE 7

Example 4 was repeated replacing isobutyl acetate with secondary butyl acetate; similar results were obtained.

EXAMPLE 8 (Comparative)

Part A

A thermoregulated titanium 6-liter autoclave equipped with a stirrer and a reflux condenser, was charged with 2500 g of a solution having the following composition (% by weight):

| $CH_3COOH$ | 88% | $Br^-$ | 0.0944% |
|---|---|---|---|
| $Co^{++}$ | 0.0181% | $H_2O$ | balance to 100% |
| $Mn^{++}$ | 0.0606% | | |

The stirrer was started, the reactor was heated to 220° C. and 6500 g/h of a mixture consisting of 75% by weight of the above solution and of 25% of paraxylene were fed; simultaneously 6500 N liters/h of air were fed so as to make the pressure reach the value of 24 kg/cm² abs. and the $O_2$ concentration in the purged gases a level equal to 3% by volume. At the same time a suspension of terephthalic acid was continuously discharged and the run was continued to 10 hours. The product continuously extracted underwent a cooling, a filtering, a washing with $CH_3COOH$ and with $H_2O$, and finally a drying under vacuum at 100° C.; after the 10 hour run the obtained terephthalic acid (yield=93.5%) contained 2100 ppm of 4-CBA and had a transmittance (see Example 1) equal to 45%.

Part B

When the product was filtered (see Part A), a reaction mother liquor was obtained which was distilled in an dehydration column. An dehydrated acetic solution containing only 3% by weight of $H_2O$, all the cobalt and all the manganese sent to the reaction and a part of the bromine was so obtained as tail product; the remaining part of bromine escaped in various manners, for example in the form of $CH_3Br$ in admixture with the distillation vapours. The reactor was charged again with 2500 g of a fresh catalytic solution, as in Part A, and 6500 g/h of a mixture consisting of 25% by weight of p-xylene and of 75% of the dehydrated solution (obtained by distillation of the mother liquor), to which suitable amounts of $Br^-$ ion were added to make up for the losses were continuously fed. It was operated according to Part A and after a 10 hour run the terephthalic acid (yield=94.5%) contained 3500 ppm of 4-CBA and had a transmittance reduced to 30%, which clearly proved the prejudicial influence exerted by the recycled impurities reacting with the dehydrated mother liquor.

EXAMPLE 9

The mother liquor coming from the filtering as per Example 8 was divided into two equal parts (H) and (K); the former (H) was dehydrated and additioned with $Br^-$, as described in Part B of Example 8, the latter (K) was heated in an evaporator until 90% of $CH_3COOH$ passed to the vapour phase. The evaporation residue was cooled down to 25° C. and the solid phase, which precipitated on cooling was separated from a liquid phase which passed to an extraction apparatus, into which isobutyl acetate and water were injected according to the weight ratio: liquid phase:isobutyl acetate:$H_2O$=1:1.5:0.5. Nearly immediately two immiscible phases were obtained, which correspond to the compositions and distribution coefficients recorded on the following table:

| Components | % by weight | | Distribution (%) | |
|---|---|---|---|---|
| | heavy phase | light phase | heavy phase | light phase |
| Water | 57.46 | 11.04 | 44 | 56 |
| Acetic acid | 33.99 | 26.38 | 16.27 | 83.03 |
| Isobutyl acetate | 4.79 | 59.67 | 1.20 | 98.80 |

-continued

| | % by weight | | Distribution (%) | |
|---|---|---|---|---|
| Components | heavy phase | light phase | heavy phase | light phase |
| Cobalt | 0.1990 | 0.0007 | 97.70 | 2.30 |
| Manganese | 0.6768 | 0.0056 | 94.76 | 5.24 |
| Bromine | 0.8058 | 0.0339 | 85 | 15 |
| Organic impurities | 2.080 | 2.870 | 9 | 91 |

The heavy phase, containing the catalyst free from impurities, was mixed with the portion (H) of mother liquid which did not undergo the extraction process. After having made up for the losses, a feed mixture consisting of 25% by weight of p-xylene was formed again and oxidation was repeated according to identical operative conditions; after a 10 hour run, the resulting terephthalic acid (yield=94%) contained 2400 ppm of 4-CBA and had a transmittance equal to 45%. That proved that it is possible to obtain satisfactory results even if more than 90% of the cobalt and manganese employed for the synthesis were recycled to the oxidation zone, without having subjected the Co and Mn compounds to any incineration or other complex treatments with acids, bases or exchange resins.

EXAMPLE 10

Example 9 was repeated, replacing isobutyl acetate with p-xylene, using the weight ratios: heavy phase:p-xylene:H₂O equal to 1:1.4:0.1; all the operations of Example 9 were repeated; after a 10-hour run the obtained terephthalic acid (with a yield of 94%) contained 2350 ppm of 4-CBA and had a transmittance of 45%. Compositions and distributions of the phases obtained through the extraction were as follows:

| | % by weight | | Distribution (%) | |
|---|---|---|---|---|
| Components | heavy phase | light phase | heavy phase | light phase |
| Water | 19.07 | 0.955 | 80.29 | 19.71 |
| CH₃COOH | 60.92 | 24.72 | 33.45 | 66.55 |
| p-xylene | 5.73 | 64.93 | 1.77 | 98.23 |
| Cobalt | 0.197 | 0.0005 | 98.77 | 1.23 |
| Manganese | 0.647 | 0.0015 | 98.88 | 1.12 |
| Bromine | 0.785 | 0.029 | 84.70 | 15.30 |
| Organic | 2.2 | 3.0 | 13 | 87 |

-continued

| | % by weight | | Distribution (%) | |
|---|---|---|---|---|
| Components | heavy phase | light phase | heavy phase | light phase |
| impurities | | | | |

We claim:
1. A method of recovering in active form the catalyst used in the synthesis of terephthalic acid from the dehydrated acetic mother liquor which comprises the steps of:
(a) removing from said mother liquor by evaporation from 70 to 90% of the acetic acid contained therein;
(b) cooling the concentrate to a temperature below 60° C.;
(c) recovering the resulting precipitate, which contains substantially all the residual terephthalic acid product, for recycle to the synthesis zone;
(d) subjecting the remaining liquid phase, which contains organic impurities, to extraction with water or with aqueous-acetic acid solutions, at a temperature of from 20° to 80° C. and in the presence of a coadjuvant in an amount by weight of 0.5 to 2.5 times the amount of said liquid phase and selected from the group consisting of p-xylene, isobutyl acetate and secondary butyl acetate;
(e) separating the heavy aqueous phase, which contains substantially all the catalyst to be recovered, from the lighter organic phase, which contains said organic impurities, and recovering said aqueous phase for recycle to the synthesis zone.
2. A method according to claim 1, characterized in that the coadjuvant is isobutyl acetate.
3. A method according to claim 1, characterized in that the coadjuvant is sec-butyl acetate.
4. A method according to claim 1, characterized in that the coadjuvant is p-xylene.
5. A method according to claim 1, characterized in that a portion equal to or higher than 95% of the heavy phase from the extraction is directly recycled to the terephthalic acid synthesis.
6. A method according to claim 1, characterized in that an amount equal to or higher than 50% of the solid phase which separates, in consequence of cooling, is directly recycled to the terephthalic acid synthesis.
7. A method according to claim 1, characterized in that the dehydrated and concentrated liquor is cooled by evaporation under vacuum between 15° and 50° C.
8. A method according to claim 1, characterized in that the coadjuvant is added in admixture with H₂O.

* * * * *